United States Patent
Rizk

(10) Patent No.: US 9,724,283 B2
(45) Date of Patent: Aug. 8, 2017

(54) HAIR CLEANSING COMPOSITION

(75) Inventor: Kirolos Rizk, Helmetta, NJ (US)

(73) Assignee: L'OREAL, Paris (FR)

(*) Notice: Subject to any disclaimer, the term of this patent is extended or adjusted under 35 U.S.C. 154(b) by 456 days.

(21) Appl. No.: 13/309,001

(22) Filed: Dec. 1, 2011

(65) Prior Publication Data

US 2013/0143784 A1 Jun. 6, 2013

(51) Int. Cl.
| | |
|---|---|
| *C11D 1/18* | (2006.01) |
| *C11D 1/83* | (2006.01) |
| *C11D 1/90* | (2006.01) |
| *C11D 1/94* | (2006.01) |
| *A61K 8/44* | (2006.01) |
| *C11D 1/12* | (2006.01) |
| *C11D 1/66* | (2006.01) |
| *A61Q 5/02* | (2006.01) |
| *A61K 8/60* | (2006.01) |

(52) U.S. Cl.
CPC ............. *A61K 8/44* (2013.01); *A61K 8/604* (2013.01); *A61Q 5/02* (2013.01); *C11D 1/126* (2013.01); *C11D 1/662* (2013.01); *C11D 1/83* (2013.01); *C11D 1/90* (2013.01); *C11D 1/94* (2013.01); *A61K 2800/262* (2013.01); *A61K 2800/30* (2013.01)

(58) Field of Classification Search
CPC ........... C11D 1/126; C11D 1/662; C11D 1/83; C11D 1/90; C11D 1/94; A61Q 5/02
USPC ....... 510/123, 124, 130, 136, 137, 138, 470, 510/499; 424/70.19, 70.21, 70.22, 70.31
See application file for complete search history.

(56) References Cited

U.S. PATENT DOCUMENTS

| | | | |
|---|---|---|---|
| 5,776,871 A * | 7/1998 | Cothran et al. | 510/122 |
| 6,218,346 B1 | 4/2001 | Sajic et al. | |
| 6,617,292 B2 * | 9/2003 | Perron et al. | 510/119 |
| 6,642,194 B2 * | 11/2003 | Harrison et al. | 510/122 |
| 2002/0019322 A1 * | 2/2002 | Nocerino et al. | 510/119 |
| 2006/0094610 A1 * | 5/2006 | Yamato et al. | 510/130 |
| 2006/0116305 A1 * | 6/2006 | Yamato et al. | 510/124 |
| 2006/0135382 A1 * | 6/2006 | Molenda | 510/119 |
| 2007/0213244 A1 * | 9/2007 | Tobita | 510/130 |
| 2011/0008275 A1 | 1/2011 | Walters et al. | |
| 2011/0059035 A1 * | 3/2011 | Bernard et al. | 424/62 |
| 2011/0082065 A1 | 4/2011 | Fevola et al. | |
| 2011/0152150 A1 * | 6/2011 | Bernard | 510/136 |
| 2011/0206629 A1 * | 8/2011 | Molenda et al. | 424/70.9 |
| 2011/0232668 A1 * | 9/2011 | Hoffmann et al. | 132/208 |

FOREIGN PATENT DOCUMENTS

| | | |
|---|---|---|
| DE | 102008038137 A1 | 2/2010 |
| EP | 1084702 A1 | 3/2001 |
| EP | 2196186 A1 | 6/2010 |
| WO | WO2010/069500 * | 6/2010 |
| WO | WO-2011130460 A1 | 10/2011 |

OTHER PUBLICATIONS

Extended European Search Report, issued in European Application No. 12853151.4, dated Apr. 15, 2015.
Notification of Transmittal of the International Search Report and the Written Opinion of the International Searching Authority, or the Declaration, International Application No. PCT/US2012/067271, mailed Feb. 5, 2013.

* cited by examiner

*Primary Examiner* — Gregory R Delcotto
(74) *Attorney, Agent, or Firm* — Polsinelli PC

(57) ABSTRACT

An aqueous hair cleansing composition comprising (a) at least one alkyl poly glucoside; (b) at least one betaine compound; and (c) at least one acyl amino acid, wherein the composition is sulfate free.

26 Claims, No Drawings

HAIR CLEANSING COMPOSITION

TECHNICAL FIELD

The present disclosure relates to compositions and methods for cleansing of keratin-based substrates such as hair. In particular, the disclosure relates to hair cleansing compositions comprising an alkyl poly glucoside, a betaine compound, and an acyl amino acid, wherein the composition is sulfate free.

BACKGROUND

Consumers of personal care products and cosmetics consider many factors in selecting products for use. Recently, certain factors have been a focus of and have driven scientific study and product development. These driving factors for hair care products include environmental impact, the extent to which the components condition hair, and the aesthetic quality of the overall product including clarity and foaming/lathering. Further, the effort towards environmental impact awareness is a universal concern and consumers are increasingly selective about the biodegradability of personal care products and cosmetics they purchase.

Hair care products which are sulfate free currently exist on the market, however, they tend to have certain undesirable properties such as lack of lathering or foaming, lack of gentle hair cleansing performance, lack of clarity especially in the presence of oils and fragrances, and poor overall viscosity.

In addition, currently available sulfate free hair care compositions require the addition of emulsifiers, thickeners, polymers, and/or hydrocolloids in order to stabilize and solubilize conditioning agents and improve viscosity. There are disadvantages to using emulsifiers, thickeners, polymers, and hydrocolloids. For example, alkoxylated emulsifiers can be eco-toxic and the process of producing them is usually harmful to the environment. Additionally, common thickeners, polymers and hydrocolloids tend to bio-accumulate and resist biodegradability, or have a negative effect on the foaming performance of the product. Thus, it is desirable to provide a composition which has improved sustainability and is biodegradable and non-toxic as compared to traditional shampoo formulations, while maintaining the favorable viscosity, foaming and cleansing properties.

Therefore, the present disclosure relates to a hair cleansing formulation that forms a visually clear cleansing composition with noticeable improvement in viscosity (gel-like appearance), stability, and solubility of conditioning agents without the need for emulsifiers such as alkoxylated surfactants or polyglycerol esters, thickeners such as glycol esters or glycol ethers, thickening or stabilizing polymers such as acrylic acid polymers and copolymers, and naturally-derived gums or hydrocolloids such as cellulose derivatives, guar or xanthan gums. Emulsifiers are generally described as ingredients that can be classified as surfactants but have properties that help form and stabilize an emulsion consisting of two phases such as oil-and-water containing phases. These emulsifiers are typically alkoxylated and have PEG, PPG, or polyglycerol functionalities. Surfactants are defined as ingredients that have the ability to modify the interface between two immiscible phases by reducing the surface tension, and serve a cleansing or detergency function.

BRIEF SUMMARY OF THE DISCLOSURE

In particular, the composition according to the disclosure demonstrates superior hair cleansing performance, excellent clarity, and improved foaming texture and abundance, even in the presence of oils and fragrance, in comparison to other sulfate free hair care formulations. Additionally, the compositions according to the disclosure are classified as "readily biodegradable".

The present disclosure relates to an aqueous hair cleansing composition comprising (a) at least one alkyl poly glucoside; (b) at least one betaine compound; and (c) at least one acyl amino acid, wherein the composition is sulfate free. In another embodiment, the present disclosure also relates to the aqueous hair cleansing composition as defined above, further comprising at least one surfactant.

Another subject of the disclosure is a method of cleansing hair, comprising applying the composition(s) described above to hair.

DETAILED DESCRIPTION OF THE DISCLOSURE

The present hair cleansing formulation forms a visually clear cleansing composition with noticeable improvement in viscosity (gel-like appearance), stability, and solubility of conditioning agents without the need for emulsifiers, thickeners, polymers, and hydrocolloids. Also, the present composition demonstrates superior hair cleansing performance, excellent clarity, and improved foaming texture and abundance, even in the presence of oils and fragrance, in comparison to other sulfate free hair care formulations. Additionally, the compositions according to the disclosure are classified as "readily biodegradable". "Readily biodegradable" is a classification term designated by the Organisation for Economic Co-operation and Development (OECD) that determines the speed of biodegradation of an organic chemical compound. Several testing methods can be used when determining the biodegradability of a compound. "Readily biodegradable" materials are tested using the stringent methods set forth by the OECD and a passing result indicates rapid biodegradation in most environments. For full information about test methods please see *Introduction to the OECD Guidelines for Testing of Chemicals Section* 3, July 2003, Organisation for Economic Co-operation and Development (OECD) available at http://www.oecd.org/dataoecd/38/2/55984432.pdf.

"At least one" as used herein means one or more and thus includes individual components as well as mixtures/combinations.

"Conditioning" as used herein means imparting to hair at least one property chosen from combability, manageability, moisture-retentivity, luster, shine, and softness. The state of conditioning is evaluated by measuring, and comparing, the ease of combability of the treated hair and of the untreated hair in terms of combing work (gm-in).

"Clear" or "excellent clarity" as used herein means visually clear. Clarity of a formulation is measured by the transmittance percentage of light with a wavelength of 700 nm by UV-Visible spectrophotometry. "Clear" samples allow for between 90% and 100% of the light to pass through the formula.

The term "sulfate free" as it is used herein means that while it is preferred that no sulfate-containing compound be present in the composition, it is possible to have very small amounts of sulfate-containing compound in the compositions of the invention provided that these amounts do not materially affect at least one, preferably most, of the advantageous properties of the shampoo of the invention. In particular, "sulfate free" means that sulfate-containing compounds can be present in the composition at an amount of less than about 2% by weight, typically less than about 1.5% by weight, typically less than about 1.0% by weight, typically less than about 0.5% by weight, typically less than about 0.1% by weight, and more typically 0% by weight, based on the total weight of the composition as a whole.

The present disclosure provides for the use of at least one alkyl poly glucoside compounds having chain lengths from $C_8$-$C_{22}$. Examples of alkyl poly glucoside compounds include but are not limited to: caprylyl/capryl glucoside, decyl glucoside, lauryl glucoside, octyl glucoside, sodium lauryl glucose carboxylate (and) lauryl glucoside, and coco glucoside. Typically, the at least one alkyl poly glucoside compound is selected from the group consisting of coco glucoside, lauryl glucoside, and decyl glucoside, and more typically lauryl glucoside.

In the present composition, at least one alkyl poly glucoside is used in an amount of from greater than 0% to about 12% by weight, typically from about 2% to about 10% by weight, and more typically from about 5% to about 10% by weight, based on the total weight of the composition as a whole.

In general, the at least one betaine compound contemplated for use in the composition includes a variety of fatty acid amide propyl betaines and sulfobetaine surfactants. Examples of betaine compounds include but are not limited to: coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, and stearyl betaine. Typically, the at least one betaine compound is selected from the group consisting of coco betaine, cocoamidopropyl betaine, behenyl betaine, capryl/capramidopropyl betaine, and lauryl betaine, and more typically cocoamidopropyl betaine.

In the present composition, at least one betaine compound is used in an amount of from greater than 0% to about 10% by weight, and typically from about 1% to about 10% by weight, and more typically from about 3.5% to about 7.5% by weight, based on the total weight of the composition as a whole.

The at least one acyl amino acid contemplated for use in the present composition includes acyl amino acid surfactants based on glycine or alanine. The salt ion attached to the at least one acyl amino acid can be sodium or potassium. Examples of acyl amino acid compounds include but are not limited to: sodium cocoyl glycinate, potassium cocoyl glycinate, and sodium lauroyl sarcosinate, sodium cocoyl alaninate, and sodium cocoyl alanine. Typically, the at least one acyl amino acid is selected from the group consisting of sodium cocoyl glycinate and potassium cocoyl glycinate, and in particular sodium cocoyl glycinate.

The at least one acyl amino acid compound is used in an amount of from greater than 0% to about 5% by weight, and typically from about 0.2% to about 5% by weight, and more typically from about 1.5% to about 3% by weight, based on the total weight of the composition as a whole.

According to the present disclosure, the hair cleansing composition has a pH of about 9 or less, and typically between about 8 and about 4.5. Additionally, the hair cleansing composition is clear and readily biodegradable.

The present hair cleansing composition has a viscosity of about 1500 cP to about 20000 cP, measured using Brookfield viscometer. Additionally, the hair cleansing composition can exclude emulsifiers, polymers, thickeners, and hydrocolloids. Typically, the present composition includes less than about 3%, less than about 1%, less than about 0.5%, or less than about 0.1% by weight of emulsifiers, polymers, thickeners, and hydrocolloids, based on the total weight of the composition as a whole. In particular, the present composition typically excludes emulsifiers, polymers, thickeners, and hydrocolloids. Examples of emulsifiers used in sulfate free shampoos which can be excluded from the present composition are laureth-9 and trideceth-12. Examples of hydrocolloids which can be excluded from the present composition are cellulose or gum derivatives such as PQ-10, guar gum, xanthan gum, which are typically used at 0.1-0.5% by weight. Examples of polymers which can be excluded from the present composition are acrylic acid based polymers such as carbomer, which are typically used at 0.1-0.5% by weight. Examples of thickeners which can be excluded from the present composition are ethoxylated fatty esters and PEG derivatives such as PEG-7 glyceryl cocoate, which are typically used at 1% by weight or more.

In another embodiment, the present composition further comprises at least one surfactant. The at least one surfactant is selected from the group consisting of sodium cocoyl isethionate and sodium lauroyl methyl isethionate. The at least one surfactant is typically used in an amount of from greater than 0% to about 10% by weight, and more typically from about 2.5% to about 7.5% by weight, based on the total weight of the composition as a whole.

The composition of the present disclosure may additionally comprise at least one ingredient chosen from conditioning agents, pH adjusting agents, preservatives, antioxidants, fragrances, and mixtures thereof.

Non-limiting examples of conditioning agents include Arginine, Asparagine, Aspartic Acid, Carnitine, Cocoyl sarcosine, Glycine, Glutamic acid, Histidine, Hydroxyproline, Acetyl Hydroxy praline, Isoleucine, Lysine, Lauroyl Lysine, Lauroyl Sarcosine, Methionine, Phenylalanine, Polylysine, Potassium Cocoyl Glutamate, Proline, Sarcosine, Serine, Rice amino acids, Silk amino acids, Wheat amino aids, Sodium Glutamate, Sodium Lauroyl Glutamate, Sodium, CA, Stearoyl sarcosine, Threonine, Tyrosine, Tryptophan, Valine, Casein, Collagen, Procollagen, Gelatin, Keratin, Glycoproteins, Hydrolyzed wheat protein, Hydrolyzed soy protein, Hydrolyzed oat protein, Hydrolyzed rice protein, Hydrolzed vegetable protein, Hydrolyzed yeast protein, Whey protein, Ginkgo Biloba Nut extract, Salix Alba (Willow) Bark Extract, Morus Alba (Mulberry) Leaf, Behentrimonium Chloride, Behenamidopropyl PG-Dimonium Chloride, Behentrimonium Methosulfate, Cocotrimonium Methosulfate, Olealkonium Chloride, Steartrimonium Chloride, Babas suamidopropalkonium Chloride, Hydroxypropyl Guar, Hydroxypropyltrimonium chloride, Laurdimonium Hydroxypropyl Hydrolyzed Soy Protein, Steardimonium Hydroxypropyl Hydrolyzed Wheat, Cocamide MIPA, Methyl Cocoate, Sodium Cocoate, Brassicamidopropyl Dimethylamine, Protein, Quaternium-22, Quaternium-27, Quaternium-87, Polyquaternium-4, Polyquaternium-6, Polyquaternium-10, Polyquaternium-11, Polyquaternium-44, Polyquaternium-67, Silicone Quaterium-8, Amodimethicone, Aminopropyldimethicone, Phenyltrimethicone, Cyclomethicone, Dimethicone, Hexyl Dimethicone, Dilinoleamidopropyl Dimthylamine Dimethicone PEG-7 Phosphate, $C_{26\text{-}28}$ Alkyl Dimethicone, PEG-8 Dimethicone, PPG-12 Dimethicone, Polysilicone-13, Trideceth-9 PG-Amodimethicone, Bis-PEG-12, Dimethicone Beeswax, Capric/Caprylic Triglyceride, Petrolatum, Mineral Oil, Lanolin Oil, *Cocos nucifera* (Coconut) Oil, *Olea Europea* (Olive) Fruit Oil, *Simmondsia Chinensis* (Jojoba) Seed Oil, *Prunus Armeniaca* (Apricot) Kernel Oil, *Crambe Abyssinica* Seed Oil, Vegetable Oil, *Zea Mays* (Corn) Oil, Acetylated Lanolin Alcohol, Cetearyl Isononanoate, Cetearyl, Ethylhexanoate, Cetearyl Palmitate, Hydrogenated Olive Oil Hexyl Esters, Triethylhexanoin, Ceramide-3, Caprylyl Glycol, Cetyl Glycol, Glycerin, Panthenol, Phytantriol, Methanediol, Inositol, PPG-35-Buteth-45, PPG-5 Butyl Ether, Cocoamidopropyl Betaine, Coco-Betaine, Cocoamidopropyl Hydroxysultaine, Lauramidopropyl Betaine, Lauryl Betaine, Oleamidopropyl Betaine, Disodium Cocoamphodiacetate, Disodium Cocoamphodipropionate, Disodium Lauroamphodiacetate, Sodium Cocoamphopropionate, Sodium Cocoamphoacetate, Alkanolamides, Acetamide MEA, Behenamide MEA, Linoleamide DEA, Linoleamide MEA, Linoleamide MIPA, Misc., Linoleic Acid, Linolenic Acid, Maltodextrin, Meadowfoam Delta Lactone, Niacin, Polyacrylate-1 Crosspolymer, Polyester-4, Pyridoxine HC1, Phytosphingosine, Salicylic Acid, Squalane, Squalene, Thiodiglycoamide, Zinc Pyrithione and mixtures thereof.

Non-limiting examples of pH adjusting agents includes potassium acetate, sodium carbonate, sodium hydroxide, phosphoric acid, succinic acid, sodium citrate, citric acid, boric acid, lactic acid, sodium hydrogen carbonate and mixtures thereof.

Non-limiting examples of preservatives include ethanol, polyvinyl alcohol, phenoxyethanol, benzyl alcohol, salicylic acid, sodium benzoate, caprylyl glycol, methyl paraben, propyl paraben, ethylhexylglycerin, 1,3-propanediol and mixtures thereof.

Suitable antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof.

The present disclosure also relates to a method of cleansing hair. The process involves contacting hair fibers with the above-described composition.

The present composition will be better understood by the examples which follow, all of which are intended for illustrative purposes only, and are not meant to unduly limit the scope of the invention in any way.

EXAMPLES yellow, gel-like compositions. Clarity of the formulation was measured by the transmittance percentage of light with a wavelength of 700 nm by UV-Visible spectrophotometry. Clear formulations allow for between 90% and 100% of the light to pass through the formula. Specifically, the clarity of formulation Example 3 is 92.4%. The viscosity of formulation Examples 1-3 varies depending on the particular combination of conditioning agents used. In particular, the viscosity of formulation Examples 1-3 ranges between 1500 cP and 20000 cP (measured using Brookfield viscometer at 50 RPM using spindle T-C). Thus, although the present composition can exclude emulsifiers, thickeners, polymers, and hydrocolloids, the formulation still exhibits a viscosity in the range of 1500 cP to about 20000 cP.

TABLE 2

| | Comparative Example 1 | |
|---|---|---|
| Attribute | Present Composition (100% biodegradable and sulfate free) Formulation Example 1 | Comparative Example Pureology Hydrate Shampoo (sulfate free; includes polymers and emulsifiers) |
| Flash Foam | comparable | comparable |
| Airy Foam | comparable | comparable |
| Abundant Foam | comparable | comparable |
| Hold/Lather Stability | comparable | comparable |
| Smooth Hair Feel in Lather | — | better |
| Rinsing Speed | comparable | comparable |
| (Rinsing) Suppleness | — | better |
| Squeaky Clean | better | — |
| Wet Hair Combing | comparable | comparable |
| Wet Hair Smoothness | comparable | comparable |
| Dry Hair Combing | comparable | comparable |
| Shine | comparable | comparable |
| Smoothness (tactile) | better | — |
| Static Fly Away | — | better |

In Comparative Example 1, various attributes of the present composition and Pureology Hydrate Shampoo were compared. Pureology Hydrate Shampoo is sulfate free but includes polymers and emulsifiers. The Test was performed on 8 panelists. As demonstrated above in Table 2, the present composition (formulation Example 1) provides for very

TABLE 1

| | Formulation Examples 1-3 | | | |
|---|---|---|---|---|
| Component | SULFATE FREE HAIR CLEANSING COMPOSITIONS Ingredient | Example 1 | Example 2 | Example 3 |
| (a) | LAURYL GLUCOSIDE | 11 | 7.15 | 7.15 |
| (b) | COCAMIDOPROPYL BETAINE | 5.7 | 3.8 | 3.8 |
| (c) | SODIUM COCOYL GLYCINATE | 3 | | 3 |
| (c) | SODIUM LAUROYL SARCOSINATE | 3 | | |
| (c) | POTASSIUM COCOYL GLYCINATE | | 3 | |
| surfactant | SODIUM COCOYL ISETHIONATE | | 4.4 | 4.4 |
| conditioning agent | COCAMIDE MIPA (and) METHYL COCOATE (and) SODIUM COCOATE | | 2 | 2 |
| conditioning agent | GLYCERIN | | 1 | 1 |
| conditioning agent | *COCOS NUCIFERA* (COCONUT) OIL | 0.25 | 0.1 | 0.1 |
| conditioning agent | BRASSICAMIDOPROPYL DIMETHYLAMINE | 1 | 0.5 | 0.5 |
| preservative | SALICYLIC ACID | 0.1 | | |
| preservative | PHENOXYETHANOL | | 0.5 | 0.5 |
| preservative | SODIUM BENZOATE | 0.1 | | |
| solvent | WATER | QS to 100 | QS to 100 | QS to 100 |

Formulation Examples 1-3 above were prepared by combining and blending the ingredients listed and heating to 50° C. All of formulation Examples 1-3 are clear, slightly similar attribute qualities as Pureology Hydrate Shampoo. Specifically, differences exist only in the attribute categories of smooth hair feel in lather, (rinsing) suppleness, smoothness, static fly away, and squeaky clean. Thus, although the present composition can exclude emulsifiers, thickeners, polymers, and hydrocolloids, overall it still provides similar attribute qualities as those compositions which include polymers and emulsifiers.

TABLE 3

Comparative Example 2

| Attribute | Present Composition (100% biodegradable and sulfate free) Formulation Example 2 | Comparative Example Fructis Pure Clean Shampoo (94% biodegradable; includes sulfates) |
|---|---|---|
| Flash Foam | comparable | comparable |
| Airy Foam | comparable | comparable |
| Abundant Foam | — | better |
| Squeaky Clean | better | — |
| Wet Hair Combing | — | better |
| Wet Hair Suppleness | comparable | comparable |
| Wet Hair Smoothness | comparable | comparable |
| Dry Hair Suppleness | comparable | comparable |
| Dry Hair Combing | comparable | comparable |
| Volume (visual) | comparable | comparable |
| Discipline | comparable | comparable |
| Smoothness (tactile) | comparable | comparable |
| Static Fly Away | comparable | comparable |

In Comparative Example 2, various attributes of the present composition and Fructis Pure Clean Shampoo were compared. Fructis Pure Clean Shampoo is 94% biodegradable but contains sulfate surfactants. As demonstrated above in Table 3, the present composition (formulation Example 2) provides for very similar attribute qualities as Fructis Pure Clean Shampoo. Specifically, differences exist only in the attribute categories of abundant foam, squeaky clean, and wet hair combing. Thus, although the present composition is sulfate free, overall it still provides similar attribute qualities as those compositions which include sulfates.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The described hereinabove are further intended to explain best modes known of practicing the disclosure and to enable others skilled in the art to utilize the disclosure in such, or other embodiments and with the various modifications required by the particular applications or uses disclosed herein. Accordingly, the description is not intended to limit the disclosure to the form disclosed herein. Also it is intended that the appended claims be construed to include alternative embodiments.

All publications, patents and patent applications cited in this specification are herein incorporated by reference, and for any and all purposes, as if each individual publication, patent or patent application were specifically and individually indicates to be incorporated by reference. In this case of inconsistencies, the present disclosure will prevail.

It is claimed:

1. An aqueous hair cleansing composition comprising:
   (a) greater than 0 to about 12% by weight of at least one alkyl poly glucoside;
   (b) greater than 0 to about 10% by weight of at least one betaine compound;
   (c) about 0.2 to about 5% by weight of at least one acyl amino acid; and
   (d) at least one surfactant selected from the group consisting of sodium cocoyl isethionate and sodium lauroyl methyl isethionate;
   wherein the composition is clear, has a viscosity of about 1500 cP to about 20000 cP, and is free of sulfates and ethoxylated fatty esters.

2. The composition as claimed in claim 1, wherein the composition has a pH of about 9 or less.

3. The composition as claimed in claim 1, wherein the composition has a pH of between about 8 and about 4.5.

4. The composition as claimed in claim 1, wherein (a) is present in an amount of from about 2 to about 10% by weight, based on the weight of the composition.

5. The composition as claimed in claim 1, wherein (a) is present in an amount of from about 5 to about 10% by weight, based on the weight of the composition.

6. The composition as claimed in claim 1, wherein (b) is present in an amount of from about 1 to about 10% by weight, based on the weight of the composition.

7. The composition as claimed in claim 1, wherein (b) is present in an amount of from about 3.5 to about 7.5% by weight, based on the weight of the composition.

8. The composition as claimed in claim 1, wherein (c) is present in an amount of from about 1.5 to about 3% by weight, based on the weight of the composition.

9. The composition as claimed in claim 1, wherein (a) is lauryl glycoside.

10. The composition as claimed in claim 1, wherein (a) is coco glucoside.

11. The composition as claimed in claim 1, wherein (a) is decyl glycoside.

12. The composition as claimed in claim 1, wherein (b) is cocoamidopropyl betaine.

13. The composition as claimed in claim 1, wherein (b) is lauryl betaine.

14. The composition as claimed in claim 1, wherein (c) is a glycine or alanine based amino acid and has a salt ion of sodium or potassium.

15. The composition as claimed in claim 14, wherein (c) is sodium cocoyl glycinate.

16. The composition as claimed in claim 14, wherein (c) is potassium cocoyl glycinate.

17. The composition as claimed in claim 14, wherein (c) is sodium cocoyl alanine.

18. The composition as claimed in claim 1, wherein the at least one surfactant is present in an amount great than 0 to about 10% by weight, based on the weight of the composition.

19. The composition as claimed in claim 1, wherein the at least one surfactant is sodium cocoyl isethionate.

20. The composition as claimed in claim 1, additionally comprising at least one ingredient selected from the group consisting of conditioning agents, pH adjusting agents, preservatives, antioxidants, fragrances, and mixtures thereof.

21. The composition as claimed in claim 1, wherein the composition includes less than about 3% by weight of emulsifiers, polymers, thickeners, and hydrocolloids, based on the weight of the composition.

22. A method of cleansing hair, comprising applying a composition according to claim 1 to hair.

23. An aqueous hair cleansing composition comprising:
(a) greater than 0 to about 12% by weight of at least one alkyl poly glucoside;
(b) greater than 0 to about 10% by weight of at least one betaine compound;
(c) greater than 0 to about 5% by weight of at least one acyl amino acid; and
(d) greater than 0% to about 10% by weight of at least one surfactant selected from the group consisting of sodium cocoyl isethionate and sodium lauroyl methyl isethionate;
wherein the composition is free of sulfates and ethoxylated fatty esters.

24. The composition of claim 23, wherein
(a) is selected from the group consisting of lauryl glycoside, coco glucoside, and decyl glycoside;
(b) is selected from the group consisting of cocoamidopropyl betaine and lauryl betaine; and
(c) is selected from the group consisting of sodium cocoyl glycinate, potassium cocoyl glycinate, and sodium cocoyl alanine; and
wherein the composition is clear.

25. The composition of claim 23 consisting essentially of:
(a) about 2 to about 10% by weight of at least one alkyl poly glucoside selected from the group consisting of lauryl glycoside, coco glucoside, and decyl glycoside;
(b) about 1 to about 10% by weight of at least one betaine compound selected from the group consisting of cocoamidopropyl betaine and lauryl betaine;
(c) about 0.2 to about 5% by weight of at least one acyl amino acid selected from the group consisting of sodium cocoyl glycinate, potassium cocoyl glycinate, and sodium cocoyl alanine; and
(d) about 2.5% to about 7.5% by weight of at least one surfactant selected from the group consisting of sodium cocoyl isethionate and sodium lauroyl methyl isethionate.

26. The composition of claim 1 wherein the composition is free of thickeners.

* * * * *